(12) United States Patent
Phillips et al.

(10) Patent No.: US 7,899,513 B2
(45) Date of Patent: Mar. 1, 2011

(54) MODULAR SOFTWARE SYSTEM FOR GUIDED RADIATION THERAPY

(75) Inventors: Stephen Chase Phillips, Woodinville, WA (US); Ryan Kempston Seghers, Kirkland, WA (US)

(73) Assignee: Calypso Medical Technologies, Inc., Seattle, WA (US)

(*) Notice: Subject to any disclaimer, the term of this patent is extended or adjusted under 35 U.S.C. 154(b) by 1461 days.

(21) Appl. No.: 11/190,194

(22) Filed: Jul. 25, 2005

(65) Prior Publication Data

US 2006/0052694 A1  Mar. 9, 2006

Related U.S. Application Data

(60) Provisional application No. 60/590,697, filed on Jul. 23, 2004.

(51) Int. Cl.
*A61B 5/05* (2006.01)
(52) U.S. Cl. ......... 600/407; 600/420; 600/424; 600/427; 600/436; 705/2; 705/3; 706/45; 706/46
(58) Field of Classification Search ............... 600/407, 600/420, 424, 427, 436; 705/2, 3; 706/45, 706/46
See application file for complete search history.

(56) References Cited

U.S. PATENT DOCUMENTS

| | | | |
|---|---|---|---|
| 3,967,161 A | 6/1976 | Lichtblau | |
| 4,023,167 A | 5/1977 | Wahlstrom | |
| 4,114,601 A | 9/1978 | Abels | |
| 4,123,749 A | 10/1978 | Hartmann et al. | |
| 4,127,110 A | 11/1978 | Bullara | |
| 4,160,971 A | 7/1979 | Jones et al. | |
| 4,222,374 A | 9/1980 | Sampson et al. | |
| 4,260,990 A | 4/1981 | Lichtblau | |
| 4,393,872 A | 7/1983 | Reznik et al. | |
| 4,618,822 A | 10/1986 | Hansen | |
| 4,633,250 A | 12/1986 | Anderson | |
| 4,643,196 A | 2/1987 | Tanaka et al. | |
| 4,696,287 A | 9/1987 | Hortmann et al. | |
| 4,795,995 A | 1/1989 | Eccleston | |
| 4,799,495 A | 1/1989 | Hawkins | |
| 4,909,789 A | 3/1990 | Taguchi et al. | |
| 4,936,823 A | 6/1990 | Colvin et al. | |
| 4,945,914 A | 8/1990 | Allen | |
| 4,994,079 A | 2/1991 | Genese | |
| 5,031,634 A | 7/1991 | Simon | |
| 5,062,847 A | 11/1991 | Barnes | |

(Continued)

FOREIGN PATENT DOCUMENTS

DE  19914455 A1  10/2000

(Continued)

OTHER PUBLICATIONS

U.S. Appl. No. 60/590,503, filed Jul. 23, 2004, Wright et al.
U.S. Appl. No. 60/590,693, filed Jul. 23, 2004, Wright et al.
U.S. Appl. No. 60/590,697, filed Jul. 23, 2004, Phillips et al.
U.S. Appl. No. 60/590,699, filed Jul. 23, 2004, Herron et al.
U.S. Appl. No. 10/416,827, filed Nov. 17, 2000, Krag.

*Primary Examiner* — Brian Casler
*Assistant Examiner* — Baisakhi Roy
(74) *Attorney, Agent, or Firm* — Perkins Coie LLP

(57) ABSTRACT

A facility for performing patient localization for radiation therapy is described. The facility activates two or more discrete software modules, and performs interactions between the activated software modules. Based upon the performed interactions, the facility performs patient localization for a radiation therapy session.

28 Claims, 9 Drawing Sheets

U.S. PATENT DOCUMENTS

| | | | |
|---|---|---|---|
| 5,095,224 A | 3/1992 | Renger | |
| 5,099,845 A | 3/1992 | Besz et al. | |
| 5,107,862 A | 4/1992 | Fabian et al. | |
| 5,142,292 A | 8/1992 | Chang | |
| 5,170,055 A | 12/1992 | Carroll et al. | |
| 5,325,873 A | 7/1994 | Hirschi et al. | |
| 5,353,804 A | 10/1994 | Kornberg et al. | |
| 5,409,004 A | 4/1995 | Sloan | |
| 5,423,334 A | 6/1995 | Jordan | |
| 5,425,367 A | 6/1995 | Shapiro | |
| 5,425,382 A | 6/1995 | Golden et al. | |
| 5,446,548 A | 8/1995 | Gerig et al. | |
| 5,509,900 A | 4/1996 | Kirkman | |
| 5,528,651 A | 6/1996 | Leksell | |
| 5,626,630 A | 5/1997 | Markowitz et al. | |
| 5,638,819 A | 6/1997 | Manwaring et al. | |
| 5,651,043 A | 7/1997 | Tsuyuki et al. | |
| 5,680,106 A | 10/1997 | Schrott | |
| 5,697,384 A | 12/1997 | Miyawaki et al. | |
| 5,707,362 A | 1/1998 | Yoon | |
| 5,707,390 A | 1/1998 | Bonutti | |
| 5,711,299 A | 1/1998 | Manwaring et al. | |
| 5,727,552 A | 3/1998 | Ryan | |
| 5,735,795 A | 4/1998 | Young et al. | |
| 5,748,767 A | 5/1998 | Raab | |
| 5,754,623 A | 5/1998 | Seki et al. | |
| 5,757,881 A | 5/1998 | Hughes | |
| 5,764,052 A | 6/1998 | Renger | |
| 5,769,861 A | 6/1998 | Vilsmeier | |
| 5,810,851 A | 9/1998 | Yoon | |
| 5,815,076 A | 9/1998 | Herring | |
| 5,840,148 A | 11/1998 | Campbell | |
| 5,868,673 A | 2/1999 | Vesely | |
| 5,879,297 A | 3/1999 | Haynor et al. | |
| 5,910,144 A | 6/1999 | Hayashi | |
| 5,928,137 A | 7/1999 | Green et al. | |
| 5,951,481 A | 9/1999 | Evans | |
| 5,957,934 A | 9/1999 | Rapoport et al. | |
| 5,989,265 A | 11/1999 | Bouquet De La Joliniere et al. | |
| 6,026,818 A | 2/2000 | Blair | |
| 6,059,734 A | 5/2000 | Yoon | |
| 6,061,644 A | 5/2000 | Leis | |
| 6,067,465 A | 5/2000 | Foo | |
| 6,076,008 A | 6/2000 | Bucholz | |
| 6,081,238 A | 6/2000 | Alicot | |
| 6,082,366 A | 7/2000 | Andra et al. | |
| 6,144,875 A | 11/2000 | Schweikard et al. | |
| 6,161,009 A | 12/2000 | Skurdal et al. | |
| 6,198,963 B1 | 3/2001 | Haim et al. | |
| 6,246,900 B1 | 6/2001 | Cosman et al. | |
| 6,307,473 B1 | 10/2001 | Zampini et al. | |
| 6,325,758 B1 | 12/2001 | Carol et al. | |
| 6,353,655 B1 | 3/2002 | Siochi | |
| 6,359,959 B1 | 3/2002 | Butler et al. | |
| 6,363,940 B1 | 4/2002 | Krag | |
| 6,371,379 B1 | 4/2002 | Dames | |
| 6,377,162 B1 | 4/2002 | Delestienne et al. | |
| 6,381,485 B1 | 4/2002 | Hunter et al. | |
| 6,385,286 B1 | 5/2002 | Fitchard et al. | |
| 6,385,288 B1 | 5/2002 | Kanematsu | |
| 6,393,096 B1 | 5/2002 | Carol et al. | |
| 6,405,072 B1 | 6/2002 | Cosman | |
| 6,416,520 B1 | 7/2002 | Kynast et al. | |
| 6,501,981 B1 | 12/2002 | Schweikard et al. | |
| 6,510,199 B1 | 1/2003 | Hughes et al. | |
| 6,526,415 B2 | 2/2003 | Smith et al. | |
| 6,535,756 B1* | 3/2003 | Simon et al. | 600/424 |
| 6,650,930 B2 | 11/2003 | Ding et al. | |
| 6,662,036 B2 | 12/2003 | Cosman | |
| 6,675,810 B2 | 1/2004 | Krag | |
| 6,698,433 B2 | 3/2004 | Krag | |
| 6,711,431 B2 | 3/2004 | Sarin et al. | |
| 6,812,842 B2 | 11/2004 | Dimmer | |
| 6,822,570 B2 | 11/2004 | Dimmer et al. | |
| 6,838,990 B2 | 1/2005 | Dimmer | |
| 6,882,947 B2 | 4/2005 | Levin | |
| 6,918,919 B2 | 7/2005 | Krag | |
| 6,934,356 B1 | 8/2005 | Satheesan et al. | |
| 6,937,696 B1 | 8/2005 | Mostafavi | |
| 6,977,504 B2 | 12/2005 | Wright et al. | |
| 6,993,112 B2 | 1/2006 | Hesse et al. | |
| 6,999,555 B2 | 2/2006 | Morf et al. | |
| 7,026,927 B2 | 4/2006 | Wright et al. | |
| 7,027,707 B2 | 4/2006 | Imaki et al. | |
| 7,072,707 B2 | 7/2006 | Galloway, Jr. et al. | |
| 7,142,905 B2 | 11/2006 | Slayton et al. | |
| 7,154,991 B2 | 12/2006 | Earnst et al. | |
| 7,174,201 B2 | 2/2007 | Govari et al. | |
| 7,206,626 B2* | 4/2007 | Quaid, III | 600/407 |
| 7,206,627 B2* | 4/2007 | Abovitz et al. | 600/407 |
| 7,213,009 B2* | 5/2007 | Pestotnik et al. | 706/46 |
| 7,221,733 B1 | 5/2007 | Takai et al. | |
| 7,289,599 B2 | 10/2007 | Seppi et al. | |
| 7,289,839 B2 | 10/2007 | Dimmer et al. | |
| 7,447,643 B1* | 11/2008 | Olson et al. | 705/2 |
| 7,557,353 B2 | 7/2009 | Black et al. | |
| 7,606,405 B2 | 10/2009 | Sawyer et al. | |
| 2002/0065461 A1 | 5/2002 | Cosman | |
| 2002/0165443 A1 | 11/2002 | Mori | |
| 2002/0193685 A1 | 12/2002 | Mate | |
| 2003/0052785 A1 | 3/2003 | Gisselberg | |
| 2003/0088178 A1 | 5/2003 | Owens et al. | |
| 2003/0192557 A1 | 10/2003 | Krag | |
| 2003/0206610 A1 | 11/2003 | Collins | |
| 2003/0206614 A1 | 11/2003 | Kendrick et al. | |
| 2004/0068182 A1 | 4/2004 | Misra | |
| 2004/0116804 A1 | 6/2004 | Mostafavi | |
| 2004/0122311 A1 | 6/2004 | Cosman | |
| 2004/0125916 A1 | 7/2004 | Herron et al. | |
| 2004/0127787 A1* | 7/2004 | Dimmer et al. | 600/424 |
| 2004/0133101 A1 | 7/2004 | Mate et al. | |
| 2004/0138555 A1 | 7/2004 | Krag | |
| 2004/0158146 A1 | 8/2004 | Mate et al. | |
| 2004/0176931 A1 | 9/2004 | Wright et al. | |
| 2005/0059884 A1 | 3/2005 | Krag | |
| 2005/0059887 A1 | 3/2005 | Mostafavi et al. | |
| 2005/0077459 A1 | 4/2005 | Engler et al. | |
| 2005/0151649 A1 | 7/2005 | Wright et al. | |
| 2005/0154280 A1 | 7/2005 | Wright et al. | |
| 2005/0154283 A1 | 7/2005 | Wright et al. | |
| 2005/0154284 A1 | 7/2005 | Wright et al. | |
| 2005/0154293 A1* | 7/2005 | Gisselberg et al. | 600/420 |
| 2005/0195084 A1 | 9/2005 | Dimmer | |
| 2005/0234332 A1 | 10/2005 | Murphy | |
| 2005/0261570 A1 | 11/2005 | Mate et al. | |
| 2006/0058648 A1* | 3/2006 | Meier et al. | 600/436 |
| 2006/0063999 A1 | 3/2006 | Herron et al. | |
| 2006/0074301 A1* | 4/2006 | Meier et al. | 600/427 |
| 2006/0074302 A1* | 4/2006 | Meier et al. | 600/427 |
| 2006/0078086 A1 | 4/2006 | Riley et al. | |
| 2006/0079764 A1 | 4/2006 | Wright et al. | |
| 2006/0100509 A1 | 5/2006 | Wright et al. | |
| 2007/0161884 A1 | 7/2007 | Black et al. | |

FOREIGN PATENT DOCUMENTS

| | | |
|---|---|---|
| EP | 0531081 A1 | 1/1992 |
| FR | 26335259 | 2/1990 |
| FR | 2686499 | 7/1993 |
| JP | 8-166446 | 6/1996 |
| WO | WO-95/25475 | 9/1995 |
| WO | WO-97/12553 | 4/1997 |
| WO | WO-98/30166 | 7/1998 |
| WO | WO-98/38908 | 9/1998 |
| WO | WO-98/40026 A | 9/1998 |
| WO | WO-99/30182 | 6/1999 |
| WO | WO-99/33406 | 7/1999 |
| WO | WO-99/40869 | 8/1999 |
| WO | WO-99/58044 | 11/1999 |
| WO | WO-99/58065 | 11/1999 |
| WO | WO-00/38579 | 7/2000 |
| WO | WO-00/51514 | 9/2000 |
| WO | WO-00/53115 | 9/2000 |
| WO | WO-00/65989 A | 11/2000 |
| WO | WO-02/39917 | 5/2002 |
| WO | WO-0239918 | 5/2002 |

* cited by examiner

| application | component | version |
|---|---|---|
| prostate | Guidance System Controller | 1.1 |
| prostate | Console UI | 1.1 |
| prostate | Tracking Station UI | 1.1 |
| prostate | System Database | 1.1 |
| prostate | Array Tracker | 1.2 |
| prostate | Front End Controller | 1.1 |
| prostate | Front End Microcontroller Program | 1.1 |
| prostate | Target Tracker | 1.1 |
| lung | Guidance System Controller | 1.2 |
| lung | Consol UI | 2.0 |
| lung | Tracking Station UI | 2.0 |
| lung | System Database | 1.1 |
| lung | Front End Controller | 1.1 |
| lung | Front End Microcontroller Program | 1.1 |
| lung | Respiration Monitor | 1.0 |
| lung | Target Tracker | 1.1 |

*FIG. 7*

| | component manifest | | |
|---|---|---|
| application | component | version |
| prostate | Guidance System Controller | 1.1 |
| lung | Guidance System Controller | 1.2 |

*FIG. 8*

MODULAR SOFTWARE SYSTEM FOR GUIDED RADIATION THERAPY

CROSS-REFERENCE TO RELATED APPLICATION(S)

This application claims the benefit of U.S. Patent Application No. 60/590,697 filed Jul. 23, 2004, which is hereby incorporated by reference in its entirety.

TECHNICAL FIELD

The present invention is directed to the field of software relating to the performance of radiation therapy.

BACKGROUND

Radiation therapy can be used to treat localized cancer. In a typical application, a radiation delivery system has an ionizing radiation device mounted to a movable gantry. The radiation delivery system controls the motion of the radiation device to direct an ionizing radiation beam to a specific point in space commonly referred to as the "machine isocenter." One aspect of radiation therapy is positioning a patient so that the patient's tumor is located at the machine isocenter. Patient positioning systems can provide information about the location of the tumor relative to the machine isocenter during patient setup procedures. Patient positioning systems use various technologies to locate the tumor, such as optically locating visual markers applied to the patient's skin, or using X-ray analysis to locate metal fiducials subcutaneously implanted in the patient.

To the extent that conventional patient positioning systems are implemented using software, such software tends to support a single medical application, such as positioning patients for treatment of prostate cancer. Such software further tends to be either (1) monolithic, so that it must be executed on a single computer system having prescribed characteristics, or (2) rigidly distributed, so that each of two or more portions of the software must each be executed on a particular single computer system having prescribed characteristics. Where such software is rigidly distributed, different portions of it are typically designed to communicate in limited predefined ways.

Such software can be difficult to adapt over time, such as to (1) change the manner in which it performs its present medical application, such as changing the technology employed to locate the tumor, or (2) support additional medical applications.

In view of the shortcomings of conventional patient positioning software described above, patient positioning software that is more readily adaptable would have significant utility.

BRIEF DESCRIPTION OF THE DRAWINGS

FIG. 7 is a table diagram showing sample contents of a component manifest data structure used in a first embodiment of the facility.

FIG. 8 is a data structure diagram showing sample contents of a component manifest data structure used in a second embodiment of the facility.

DETAILED DESCRIPTION

Figure 1:
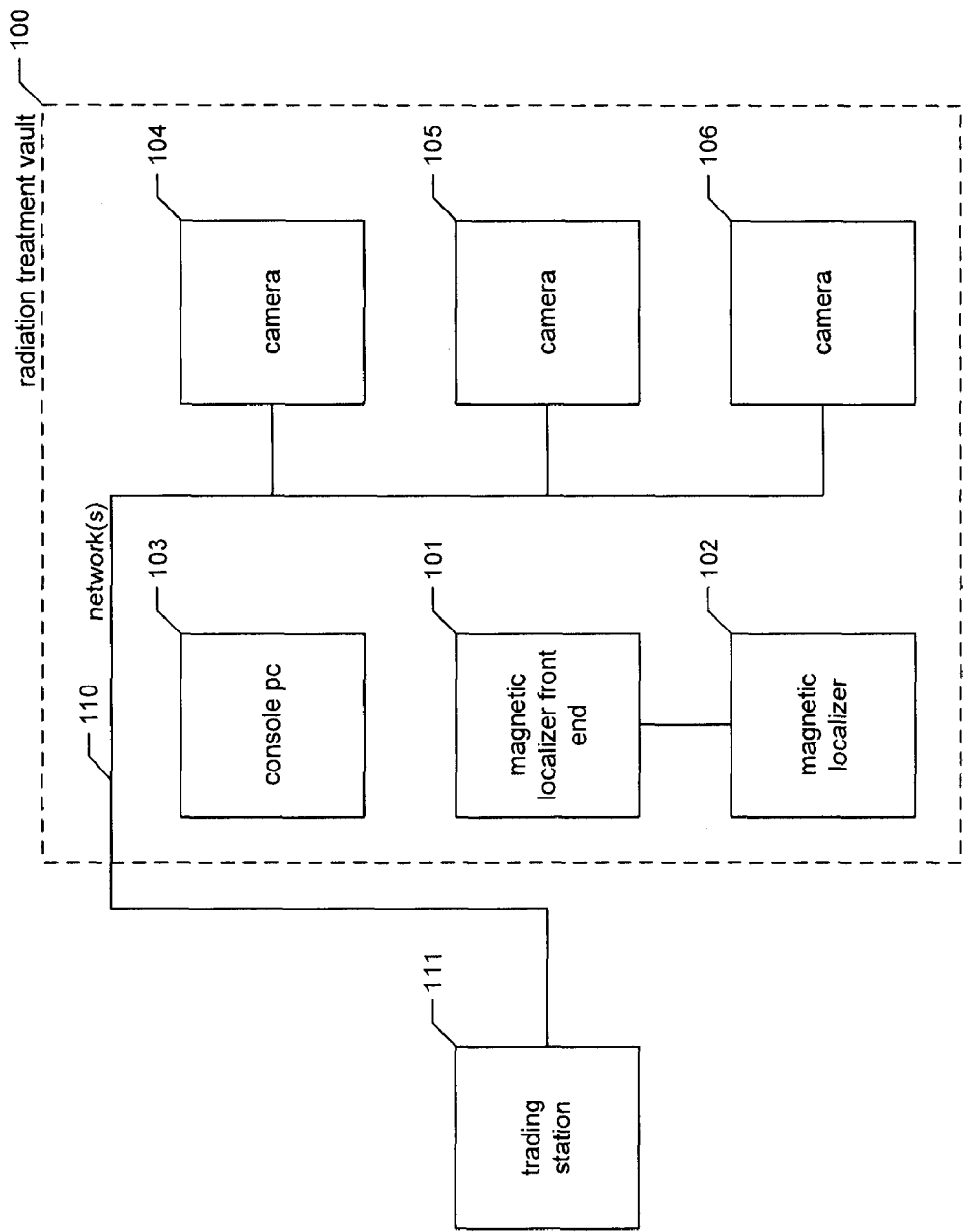
FIG. 1 is a network diagram showing computer systems and other hardware devices used by the facility.

A modular software facility for performing patient localization and/or location tracking during radiation therapy ("the facility") is described. In some embodiments, the facility employs a set of distinct software components that interact in order to collectively perform the tracking function. In some embodiments, these components are substitutable software elements, each performing a different role and providing one or more functions. Components typically isolate dependencies of various types to a minimum number of components, abstracting their detailed operation away from their higher level function. Components typically communicate in well-defined ways, including via a publish and subscribe mechanism.

In some embodiments, the components communicate using standardized mechanism, such as a publish-and-subscribe mechanism. In these embodiments, the dependencies and interactions between components are defined based upon what information each component provides ("publishes"), and what information each component consumes ("subscribes to"). By limiting the dependencies that components may have on one another, this design minimizes the risk that a re-implemented component will fail to interact properly with other existing components. For example, this design may be used to isolate dependencies on the particular technology used to locate the tumor to a small subset of the components, so that the remaining components are free of dependencies on the technology used. If the technology used is subsequently changed, the software facility could be adapted to the new technology by re-implementing only the subset of components. The use of a publish-and-subscribe mechanism enables the set of components consuming particular information from a particular publisher component to expand or contract without any special processing by the publisher component.

In some embodiments, the facility utilizes a publish-and-subscribe mechanism that supports location transparency, such as publish-and-subscribe using NET remoting. In these embodiments, many of the components can be executed on any of a set of connected computer systems, providing a measure of flexibility in the deployment of the facility.

In some embodiments, an update to the facility is performed by replacing a proper subset of the facility's components with re-implemented versions of these components, without re-implementing the remaining components.

In some embodiments, the facility may provide a number of different medical applications, such as patient tracking during radiation therapy for prostate cancer, lung cancer, breast cancer, cancer of the head and neck, liver cancer, pancreatic cancer, cervical cancer, orthopedic cancer, etc. In some such embodiments, each medical application is constituted of a particular set of components. For example, a particular medical application could add a new component not present in other medical applications, or replace a component present in other medical applications with a new implementation of the component. A particular medical application may also include additional hardware to be connected to the computing system. In these embodiments, the facility provides particular medical application by invoking the particular components used by the medical application. In such embodiments, the different applications may be distributed to customers separately. As one example, a new application may be distributed to a customer by providing a customer with a copy of each module.

In some embodiments, the facility may provide a number of different activities relating to a localization and tracking system, including patient set up, patient treatment, patient biofeedback monitoring, patient treatment rehearsal, retrospective treatment data review, treatment data reporting, etc. In various embodiments, these activities are performed as described in U.S. patent application Ser. No. 11/189,542 filed concurrently herewith and entitled USER INTERFACE FOR GUIDED RADIATION THERAPY, which is hereby incorporated by reference in its entirety. In some embodiments, each activity is constituted of a particular set of components. In such embodiments, the different activities may be distributed to customers separately.

In some embodiments, the facility may enable the tracking system to interact with a number of add-on functionalities, such as an accessory for positioning a couch or other structure supporting the patient; an accessory for controlling the intensity of the radiation beam; an accessory for controlling the shape of the radiation beam; an accessory for controlling devices securing the treatment room; an accessory for collecting biofeedback input, such as pulse or respiration; an accessory for performing pre-treatment or intra-treatment imaging; an accessory for supporting the correlation of time-index data for multiple sources; a quality assurance package for one or more accessories, etc. In some such embodiments, each such add-on functionality is constituted of a particular set of components. In some embodiments, the different add-on functionalities may be distributed to customers separately.

In some embodiments, the facility is directed towards tracking a target, i.e., measuring the position and/or the rotation of a target in substantially real time, in a patient in medical applications. In some such embodiments, the facility collects position data of a marker that is substantially fixed relative to the target, determines the location of the marker in an external reference frame (i.e., a reference frame outside the patient), and provides an objective output in the external reference frame that is responsive to the location of the marker. The objective output is repeatedly provided at a frequency/periodicity that adequately tracks the location of the target in real time within a clinically acceptable tracking error range. As such, such tracking enables accurate tracking of the target during diagnostic, planning, treatment or other types of medical procedures. In many specific applications, the objective output is provided within a suitably short latency after collecting the position data and at a sufficiently high frequency to use the data for such medical procedures.

In some or all of the above-described embodiments, the facility provides significant flexibility and adaptability to a system for tracking patient position for radiation therapy.

FIG. 1 is a network diagram showing computer systems and other hardware devices used by the facility. A number of the computer systems and devices are connected by one or more data networks 110. These include a magnetic localizer front end 101 for controlling a magnetic localizer device 102. A tracking station 111 combines information from the magnetic localizer front end, as well as one or more camera, such as cameras 104-106. The tracking station also provides a visual user interface. A console PC 103 provides an additional visual user interface. Computer systems and devices 101-106 are typically located inside a radiation treatment vault 100, while the tracking station 111 is located outside. Those skilled in the art will appreciate that the facility may use sets of devices that differ from those shown here, including sets of devices that omit devices shown here, those that include devices not shown here, and/or those that combine or divide the functionality of devices shown here. One or more suitable, exemplary patient localization systems are described in the following, each of which is hereby incorporated by reference in its entirety: U.S. patent application Ser. No. 10/334,700, entitled PANEL-TYPE SENSOR/SOURCE ARRAY ASSEMBLY, filed Dec. 30, 2002; U.S. patent application Ser. No. 09/877,498, entitled GUIDED RADIATION THERAPY SYSTEM, filed Jun. 8, 2001; U.S. patent application Ser. No. 10/679,801, entitled METHOD AND SYSTEM FOR MARKER LOCALIZATION, filed Oct. 6, 2003; U.S. patent application Ser. No. 10/746,888, entitled IMPLANTABLE MARKER WITH WIRELESS SIGNAL TRANSMITTAL, filed Dec. 24, 2003; and U.S. patent application Ser. No. 10/749,478, entitled RECEIVER USED IN MARKER LOCALIZATION SENSING SYSTEM, filed Dec. 31, 2003.

Figure 2:
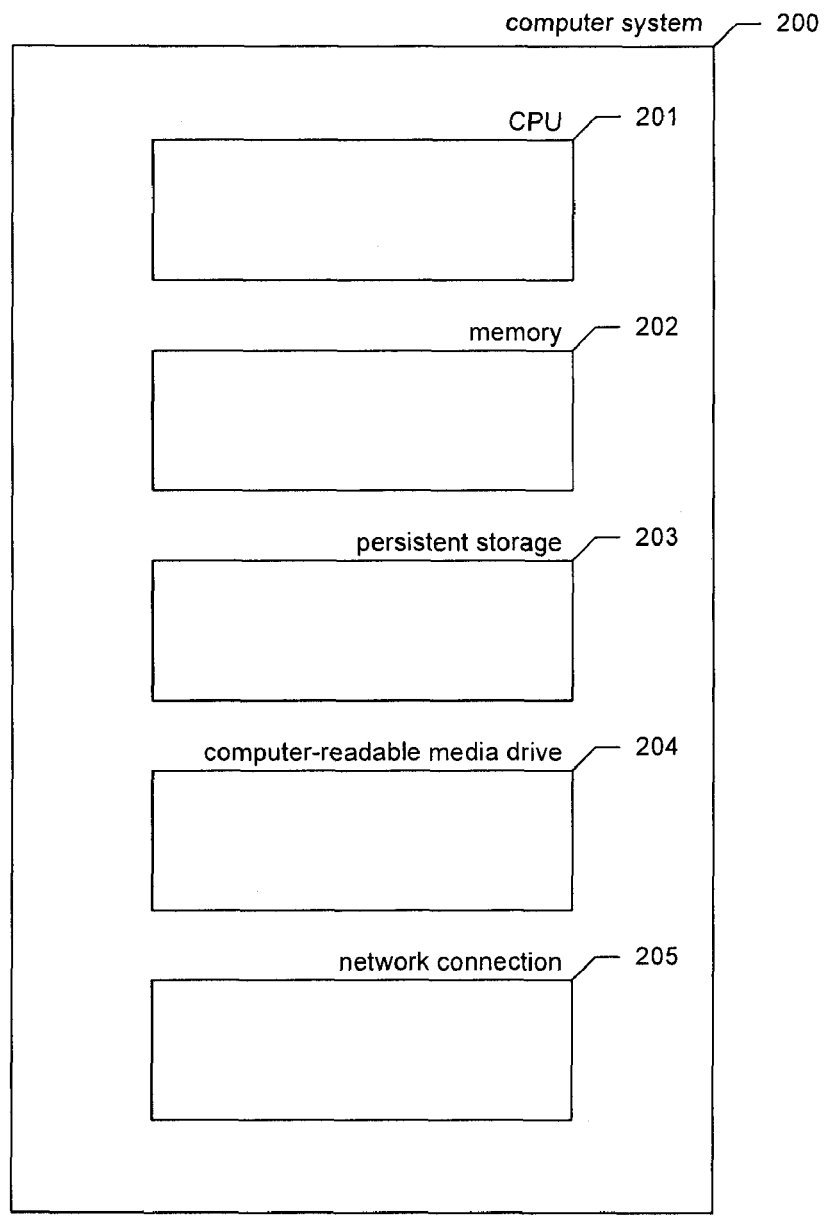
FIG. 2 is a block diagram showing some of the components typically incorporated in at least some of the computer systems and other devices on which the facility executes.

FIG. 2 is a block diagram showing some of the components typically incorporated in at least some of the computer systems and other devices on which the facility executes. These computer systems and devices 200 may include one or more central processing units ("CPUs") 201 for executing computer programs; a computer memory 202 for storing programs and data—including data structures—while they are being used; a persistent storage device 203, such as a hard drive, for persistently storing programs and data; a computer-readable media drive 204, such as a CD-ROM drive, for reading programs and data stored on a computer-readable medium; and a network connection 205 for connecting the computer system to other computer systems, such as via the Internet, to exchange programs and/or data—including data structures. While computer systems configured as described above are typically used to support the operation of the facility, one of ordinary skill in the art will appreciate that the facility may be implemented using devices of various types and configurations, and having various components.

Figure 3:
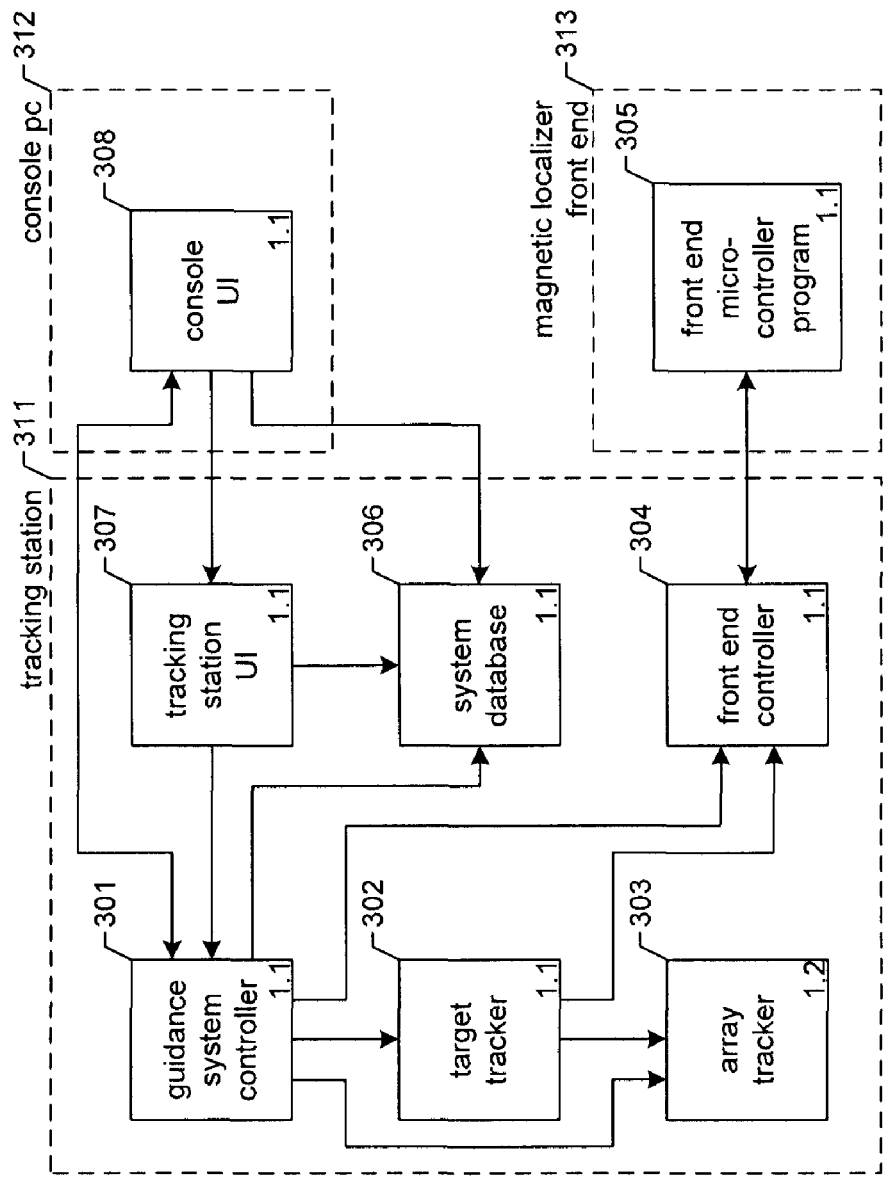
FIG. 3 is a component diagram showing a typical set of components used by the facility to provide a medical application for tracking patient location during radiation treatment delivered to a prostate tumor.

FIG. 3 is a component diagram showing a typical set of components used by the facility to provide a medical application for tracking patient location during radiation treatment delivered to a prostate tumor. Those skilled in the art will appreciate that the facility could provide this application using a different set of components, such as a set of components that includes components not shown, a set of components that omits shown components, and/or a set of components in which the functionality of components is consolidated or divided.

FIG. 3 shows components 301-308, as well as dependencies between these components. A Guidance System Controller component 301 is the top-level component for the facility. The Guidance System Controller component acts as a registry for the various services, and represents the entire facility. A Target Tracker component 302 tracks the target isocenter of the patient by integrating the location of a sensor array provided by an Array Tracker component 303 with magnetic transponder locations provided by a Front-End Controller component 304. Target isocenter tracking information may be used in a variety of ways, such as those described in U.S. Patent Application No. 60/590,693 filed Jul. 23, 2004, U.S.

patent application Ser. No. 11/190,205 filed concurrently herewith and entitled DATA PROCESSING FOR REAL-TIME TRACKING OF A TARGET IN RADIATION THERAPY, U.S. Patent Application No. 60/590,503 filed Jul. 23, 2004, and U.S. patent application Ser. No. 11/189,431, filed concurrently herewith and entitled DYNAMIC/ADAPTIVE TREATMENT PLANNING FOR RADIATION THERAPY, each of which is hereby incorporated by reference in its entirety. The Target Tracker component outputs the location of the treatment isocenter relative to the machine isocenter, and publishes transponder locations and sensor array locations in the same coordinate system. The Array Tracker component 303 controls and provides access to cameras used to track the location of the sensor array, as well as a hub, and a vision tracking library used to analyze the input from the cameras. The Front-End Controller component 304 controls and provides information from a front-end Microcontroller Program component 305. The Front-End Controller component may include and/or use a front-end interface and a magnetic localization algorithm library. The Front-End Controller component provides services, including logging, to the front-end microcontroller program component. The Front-End Controller component provides transponder locations relative to the sensor array to various subscribers. The Front-End Microcontroller Program component drives a sensor array to acquire raw magnetic transponder data. A System Database component 306 stores and provides access to system data such as patient records. A Tracking Station UI component 307 provides a graphical user interface providing capabilities such as patient data access, treatment room monitoring, and reporting.

Console UI component 308 provides a graphical user interface for users in the radiation treatment vault, including patient session management, array positioning, tracking, quality assurance testing, and calibration. Sample behaviors provide by such UI components are described in U.S. Patent Application No. 60/590,699 filed Jul. 23, 2004 entitled USER INTERFACE FOR GUIDED RADIATION THERAPY, and U.S. patent application Ser. No. 11/189,542, filed concurrently herewith and entitled USER INTERFACE FOR GUIDED RADIATION THERAPY, each of which is incorporated herein by reference in its entirety.

Component 305 typically executes on the magnetic localizer front end component 313, typically located inside the radiation treatment vault. Component 308 typically executes on the console PC 312, typically located inside the radiation treatment vault. Components 301, 302, 303, 304, 306, and 307 typically execute on the tracking station 311, typically located outside the radiation treatment vault.

The direction(s) of the arrows between pairs of components indicate the dependency relationship(s) between the components. For example, the double-headed arrow between components 301 and 308 indicates both that component 301 has a dependency on component 308 and component 308 has a dependency on component 301. The single-headed arrow between components 301 and 307 indicates that component 307 has a dependency on component 301. The design for some embodiments omits various inter-component dependencies shown in FIG. 3, such as the dependency of component 301 on components 303 and 304. In some embodiments, dependencies between components indicate a publish/subscribe relationship between the components. For instance, the dependency of component 307 on component 301 may indicate that component 307 subscribes to data published by component 301. In some embodiments, these dependencies are also used as a basis for module invocation, as is discussed in greater detail below. FIG. 3 further identifies a version number of each component, shown in a circle inside the component's rectangle. For example, FIG. 3 shows that the guidance system controller component 301 is of version 1.1.

Figure 4:
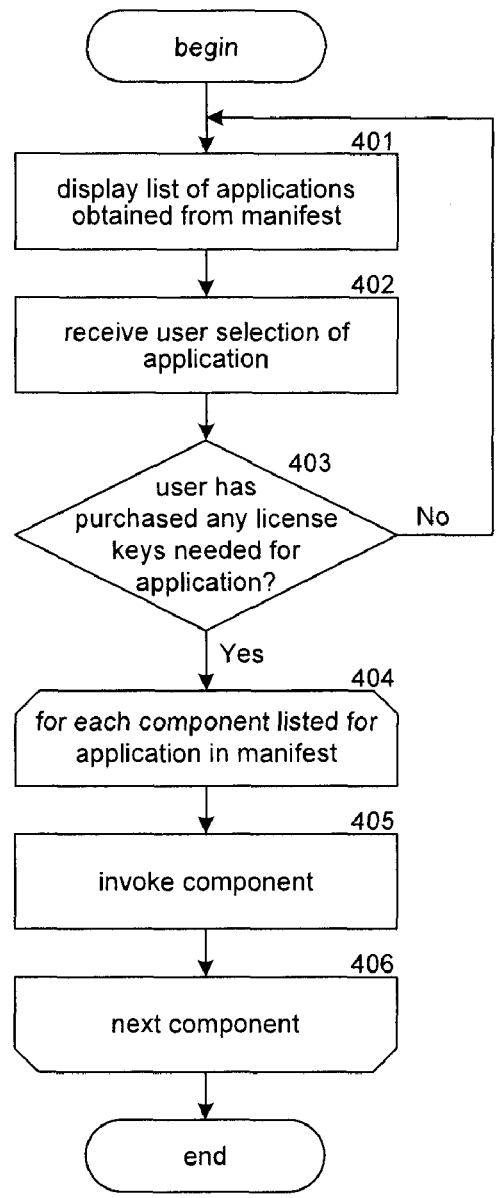
FIG. 4 is a flow diagram showing steps typically performed by the facility in order to launch a particular application.

FIG. 4 is a flow diagram showing steps typically performed by the facility in order to launch a particular application. In step 401, the facility displays a list of applications obtained from a manifest data structure, discussed below in conjunction with FIGS. 7 and 8. In step 402, the facility receives a user selection of one of the applications displayed in step 401. In step 403, if the user has purchased any license keys needed for the application, then the facility continues in step 404, else the facility continues in step 401. In some embodiments, the facility omits step 403, and does not enforce a license key requirement in order to launch an application. In steps 404-406, the facility loops through each component listed in the manifest for the selected application. In step 405, the facility invokes the current component, such as is described below in connection with FIG. 5. In step 406, if additional components remain to be processed, then the facility continues step 404 to process the next component, else these steps conclude.

Figure 5:
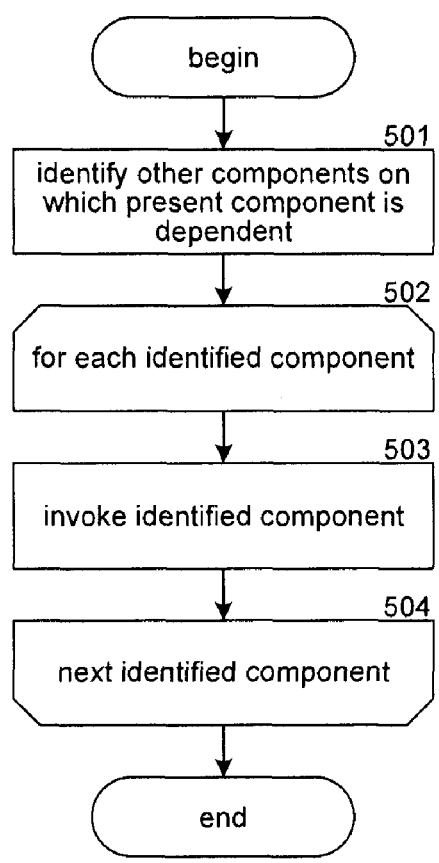
FIG. 5 is a flow diagram showing steps typically performed by the facility in order to invoke an individual component.

FIG. 5 is a flow diagram showing steps typically performed by the facility in order to invoke an individual component. In step 501, the facility identifies other components upon which the present component is dependent. In steps 502-504, the facility loops through each identified component. In step 503, the facility invokes the identified component. In step 504, if additional identified components remain to be processed, then the facility continues to step 502 to process the next identified component, else these steps conclude.

Figure 6:
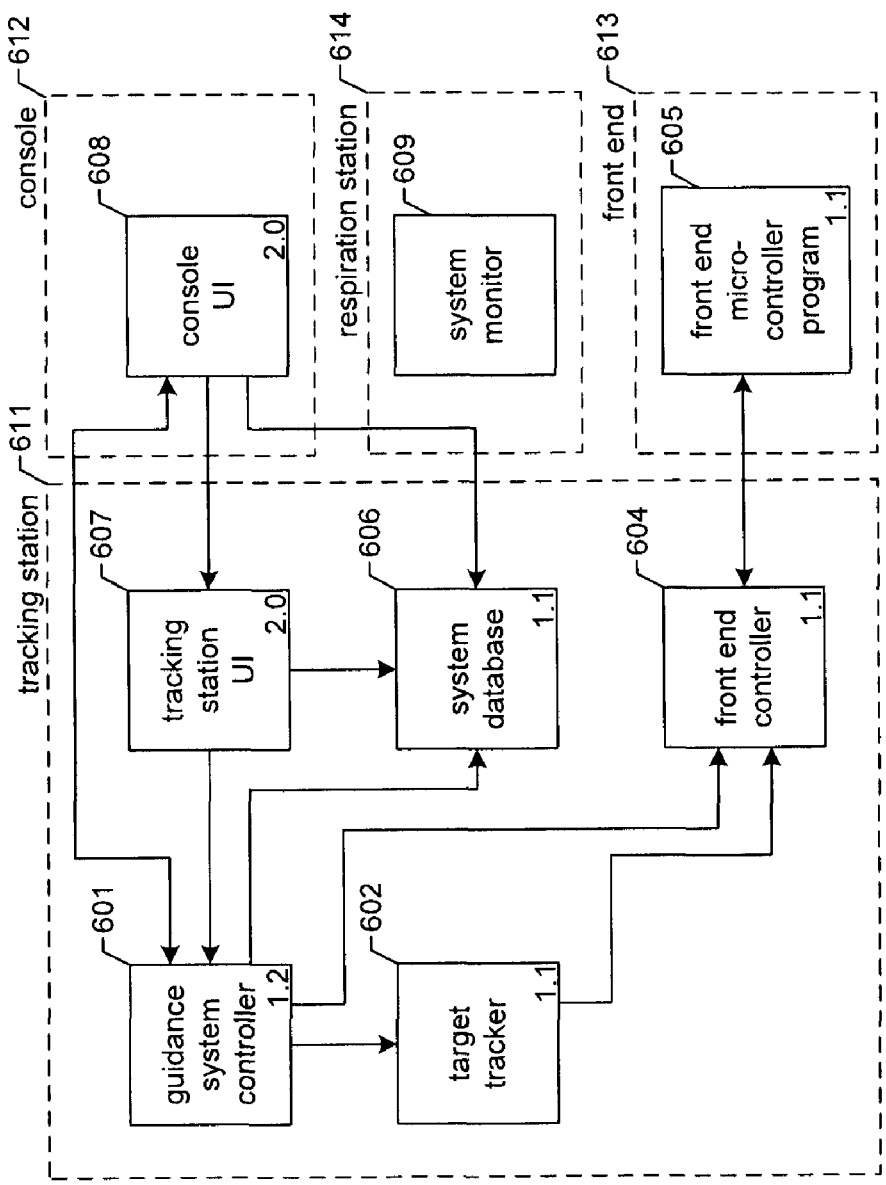
FIG. 6 is a component diagram showing a set of components typically used by the facility to provide a medical application for tracking patient location during radiation treatment of a lung tumor.

FIG. 6 is a component diagram showing a set of components typically used by the facility to provide a medical application for tracking patient location during radiation treatment of a lung tumor. By comparing FIG. 6 with FIG. 3, one can discern that there is intersection between components used to provide the prostate application and components used to provide the lung application. The differences are as follows: Array Tracker component 303 shown in FIG. 3 is omitted from FIG. 6; Guidance System Controller component 601 shown in FIG. 1 has version number 1.2 as opposed to version number 1.1 of Guidance System Controller component 301 shown in FIG. 3; the Tracking Station UI component 607 shown in FIG. 6 is of version 2.0, whereas the Tracking Station UI component 307 shown in FIG. 3 is of version 1.1; the console UI component 608 shown in FIG. 6 is of version 2.0, whereas the console UI component 308 shown in FIG. 3 is of version 1.1; and an additional respiration monitor component 609, executing on a new respiration station computer station 614, has been added.

FIG. 7 is a table diagram showing sample contents of a component manifest data structure used in a first embodiment of the facility. Component Manifest 700 is a table made up of rows 701-716, each corresponding to a component employed in a particular application. In particular, component manifest 700 contains a row for every component used in each application. Each row is divided into an application column 751 identifying the application, a component column 752 identifying the component, and a version number column 753 identifying the version. For example, row 701 indicates that the prostate application uses version 1.1 of the guidance system controller component. In using component manifest 700, the facility would invoke the versions of the components shown in row 701-708 directly as part of invoking the prostate application.

FIG. 8 is a data structure diagram showing sample contents of a component manifest data structure used in a second embodiment of the facility. The component manifest data structure 800 is similar to component manifest 700, except that fewer components are identified for each application. For instance, component manifest 800 contains a single row 801 identifying a component for the prostate application. When component manifest 800 is used, version 1.1 of the Guidance System Controller component is directly invoked as part of launching the prostate application. When the Guidance System Controller component is invoked, it in turn invokes the components upon which it has dependencies, until all of the components needed for the prostate application are invoked.

Figure 9:
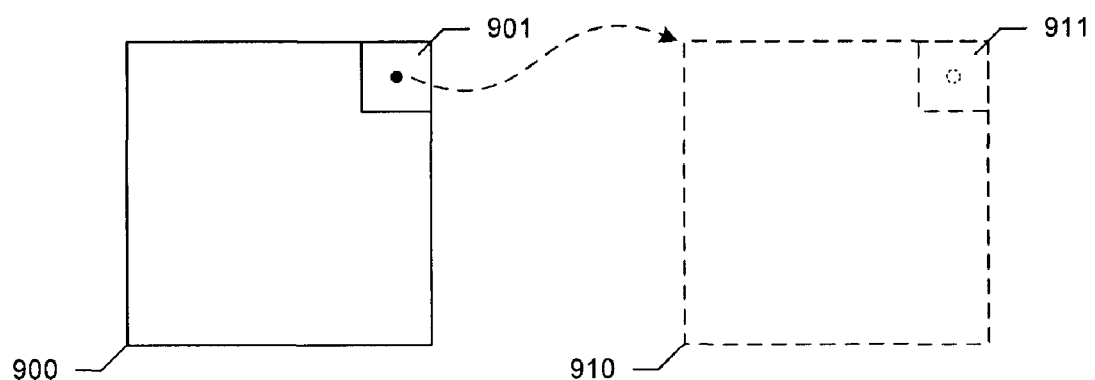
FIG. 9 is a data structure diagram showing a component dependency used in recursive invocation of components.

FIG. 9 is a data structure diagram showing a component dependency used in the recursive invocation of components discussed above in conjunction with FIG. 8. A first component 900 contains a reference 901 to a second component 910. In connection with loading the first component, the facility uses the reference from the first component to the second component to invoke the second component. If the second component contains one or more of its own references 911, the facility in turn uses the references 911 to invoke the depended-on components. The references may be stored either internally or externally to the components, or both. The references may identify the referred to components in a variety of ways, such as using a file name, a fully-qualified path, a global unique identifier, a name and version number, or any of a number of other types of references.

The localization system and at least one marker enables real time tracking of a target relative to a machine isocenter or another external reference frame outside of the patient during treatment planning, set up, radiation sessions, and at other times of the radiation therapy process. In many embodiments, real time tracking means collecting position data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time).

For example, several embodiments of real time tracking are defined as determining the locations of the markers and calculating the location of the target relative to the machine isocenter at (a) a sufficiently high frequency so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the location system 10 calculates the absolute position of each individual marker 40 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real time tracking can further mean that the location system 10 provides the absolute locations of the markers and/or the target to a memory device, user interface, linear accelerator or other device within a latency of 10 ms to 5 seconds from the time the localization signals were transmitted from the markers. In more specific applications, the location system generally provides the locations of the markers and/or target within a latency of about 20-50 ms. The location system accordingly provides real time tracking to monitor the position of the markers and/or the target with respect to an external reference frame in a manner that is expected to enhance the efficacy of radiation therapy because higher radiation doses can be applied to the target and collateral effects to healthy tissue can be mitigated.

Alternatively, real-time tracking can further be defined by the tracking error. Measurements of the position of a moving target are subject to motion-induced error, generally referred to as a tracking error. According to aspects of the present invention, the localization system and at least one marker enable real time tracking of the target relative to the machine isocenter or another external reference frame with a tracking error that is within clinically meaningful limits.

Tracking errors are due to two limitations exhibited by any practical measurement system, specifically (a) latency between the time the target position is sensed and the time the position measurement is made available, and (b) sampling delay due to the periodicity of measurements. For example, if a target is moving at 5 cm/s and a measurement system has a latency of 200 ms, then position measurements will be in error by 1 cm. The error in this example is due to latency alone, independent of any other measurement errors, and is simply due to the fact that the target has moved between the time its position is sensed and the time the position measurement is made available for use. If this exemplary measurement system further has a sampling periodicity of 200 ms (i.e., a sampling frequency of 5 Hz), then the peak tracking error increases to 2 cm, with an average tracking error of 1.5 cm.

In some embodiments, the facility uses structure and/or techniques described in U.S. patent application Ser. No. 11/166,801, filed on Jun. 24, 2005, which is hereby incorporated by reference in its entirety.

It will be appreciated by those skilled in the art that the above-described facility may be straightforwardly adapted or extended in various ways. For example, the facility may be used in conjunction with a wide variety of components, executing on a wide variety of computer systems or other devices, and may provide a variety of different medical applications relating to radiation therapy. While the foregoing description makes reference to preferred embodiments, the scope of the invention is defined solely by the claims that follow and the elements recited therein.

We claim:

1. A method in a computing system for performing patient localization for radiation therapy, comprising:

activating in the computing system a plurality of discrete software modules, wherein the discrete software modules provide at least two types of radiation therapy applications and each radiation therapy application is comprised of a different subset of the plurality of discrete software modules, and wherein the activating includes invoking a first software module that invokes a subset of the plurality of discrete software modules upon which the invoked software module has dependencies for a selected type of radiation therapy application;

performing interactions between the activated software modules for the selected type of radiation therapy application;

based on the performed interactions, performing patient localization for a radiation therapy session; and based on the performed interactions, performing patient tracking for the radiation therapy session, wherein the performed patient tracking is performed while a radiation dosage is being delivered to a patient.

2. The method of claim 1 wherein the at least two types of radiation therapy applications are selected from the group consisting of: a prostate cancer radiation therapy application, a lung cancer radiation therapy application, a breast cancer radiation therapy application, a head cancer radiation therapy application, a neck cancer radiation therapy application, a liver cancer radiation therapy application, a pancreatic cancer radiation therapy application, a cervical cancer radiation therapy application, and a orthopedic cancer radiation therapy application.

3. The method of claim 1 wherein performing patient tracking provides a location in a patient relative to an external reference frame at a frequency such that the tracking error is less than five millimeters.

4. The method of claim 1 wherein the first software module is activated in a first computer system, and wherein a second software module is activated in a second computer system that is connected to the first computer system by a network, and wherein at least one of the performed interactions is an interaction between the first and second software module that traverses the network between the first and second computer systems.

5. The method of claim 1 wherein the modules installed include:
   a fiducial interrogation module that drives a sensor array to interrogate a set of one or more transponders;
   a controller module that controls the transponder interrogation module and determines the location of each transponder of the set; and
   a patient tracking module that determines the location of a patient treatment site relative to a treatment delivery isocenter.

6. The method of claim 5 wherein the modules installed further include:
   a tracking station user interface for displaying patient localization information;
   a database module for storing patient localization information; and
   a localization device tracking module for tracking the location of a patient localization device relative to the location the treatment delivery isocenter.

7. The method of claim 6 wherein the modules installed further include:
   a central module representing all of the installed software modules; and
   a console user interface for displaying patient localization information to an occupant of a treatment chamber in which radiation therapy is delivered.

8. The method of claim 1 wherein the modules installed include a distinguished module specific to a radiation therapy treatment site.

9. The method of claim 1 wherein the modules installed include a distinguished module specific to a radiation therapy treatment activity.

10. The method of claim 1 wherein the modules installed include a distinguished module specific to a radiation therapy treatment device.

11. The method of claim 10 wherein the radiation therapy treatment device is a specific device.

12. The method of claim 10 wherein the radiation therapy treatment device is a specific class of devices.

13. The method of claim 12 wherein the modules installed further include a second distinguished module corresponding to a specific device among the class of devices.

14. The method of claim 13 wherein the second distinguished module is comprised of code.

15. The method of claim 13 wherein the second distinguished module is comprised of parameter values read and applied by the distinguished module.

16. The method of claim 1 wherein at least a portion of the interactions are performed using a publish and subscribe mechanism.

17. The method of claim 16 wherein at least one of the performed interactions is a publication of distinguished information from a publisher module possessing the distinguished information to at least one subscriber module that has subscribed for the distinguished information.

18. The method of claim 1 wherein at least a portion of the interactions are performed using .NET remoting.

19. The method of claim 1 wherein continuous patient localization is performed for a radiation therapy session.

20. The method of claim 1 wherein all interactions between the modules are performed using a publish and subscribe mechanism.

21. The method of claim 1 wherein the computing system is a distributed computing system comprising at least a first node and a second node, and wherein a first of the software modules is activated in the first node, and wherein a second of the software modules is activated in the second node, and wherein inter-node interactions are performed between the first and second software modules.

22. The method of claim 1 wherein the computing system is a distributed computing system comprised of a plurality of nodes in which software modules may be activated, and wherein at least a portion of the modules may be activated on two or more different nodes of the distributed computing system.

23. The method of claim 1 wherein at least one of the activated software modules operates in a way that is dependent upon the technological approach used to perform patient localization, and wherein at least one of the activated software modules operates in a way that is not dependent on the technological approach used to perform patient localization.

24. The method of claim 1 wherein the first software module determines a result from received data, and wherein a second software module distinct from the first software module independently determines its own result from the received data in order to validate the result of the first software module.

25. The method of claim 1 wherein the first software module determines a result from received data, and wherein a second software module performs at least one back check on the result produced by the first module to validate the result produced by the first module.

26. The method of claim 1 wherein the interactions are performed in a manner that is independent of hardware architecture and operating system identity.

27. A non-transitory computer-readable storage medium whose contents cause a computing system to perform a method for performing patient localization for radiation therapy, comprising:
   activating in the computing system a plurality of discrete software components, wherein the discrete software components provide at least two types of radiation therapy applications and each radiation therapy application is comprised of a different subset of the plurality of discrete software components, and wherein the activating includes invoking a first software component that invokes a subset of the plurality of discrete software components upon which the invoked software component has dependencies for a selected type of radiation therapy application;
   performing interactions between the activated software components for the selected type of radiation therapy application; and
   based on the performed interactions, performing patient localization for a radiation therapy session.

28. A computing system for performing patient localization, comprising:

two or more networked nodes; and a localization initiation subsystem that, for each of a plurality of discrete software modules, activates the software module in one of the nodes, enabling the activated software modules to perform interactions through which patient localization is performed for a radiation therapy session, wherein the discrete software modules provide at least two types of radiation therapy applications and each radiation therapy application is comprised of a different subset of the plurality of discrete software modules, and wherein the activation of the software module in one of the nodes includes invoking the software module which then invokes a subset of the plurality of discrete software modules upon which the invoked software module has dependencies for a selected type of radiation therapy application.

* * * * *